United States Patent
Farritor et al.

(10) Patent No.: US 8,577,647 B2
(45) Date of Patent: Nov. 5, 2013

(54) VERTICAL TRACK MODULUS TRENDING

(75) Inventors: Shane M. Farritor, Lincoln, NE (US); Sheng Lu, Lincoln, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 167 days.

(21) Appl. No.: 13/046,064

(22) Filed: Mar. 11, 2011

(65) Prior Publication Data

US 2011/0166827 A1    Jul. 7, 2011

Related U.S. Application Data

(63) Continuation of application No. 12/206,345, filed on Sep. 8, 2008, now Pat. No. 7,937,246, which is a continuation-in-part of application No. 12/049,805, filed on Mar. 17, 2008, now Pat. No. 7,920,984.

(60) Provisional application No. 60/970,740, filed on Sep. 7, 2007, provisional application No. 60/894,983, filed on Mar. 15, 2007.

(51) Int. Cl.
*G01C 22/00*    (2006.01)

(52) U.S. Cl.
USPC .............. 702/189; 702/150; 701/49; 73/81; 356/614

(58) Field of Classification Search
USPC .......... 702/150, 189; 73/81; 356/614; 701/49
See application file for complete search history.

(56) References Cited

U.S. PATENT DOCUMENTS

| | | | |
|---|---|---|---|
| 3,960,005 A | 6/1976 | Vezina | |
| 4,010,636 A | 3/1977 | Clark et al. | |
| 4,283,953 A | 8/1981 | Plona | |
| 4,435,984 A | 3/1984 | Gruber | |
| 5,020,371 A | 6/1991 | Panetti | |
| 5,335,184 A | 8/1994 | Hildebrand | |

(Continued)

FOREIGN PATENT DOCUMENTS

| | | |
|---|---|---|
| EP | 2182351 A1 | 5/2010 |
| JP | 07174643 | 7/1995 |
| SU | 1801844 | 3/1993 |

OTHER PUBLICATIONS

Lu, Sheng et al., "Exception Criteria in Vertical Track Deflection and Modulus", 2007 ASME/IEEE Joint Rail Conference & Internal Combustion Engine Spring Technical Conference, Mar. 13, 2007, Pueblo, CO USA, 12 pages.

(Continued)

*Primary Examiner* — Jonathan C Teixeira Moffat
*Assistant Examiner* — Hien Vo
(74) *Attorney, Agent, or Firm* — Davis, Brown, Koehn, Shors & Roberts, P.C.; Sean D. Solberg

(57) ABSTRACT

Systems and methods for determining a trend in vertical track modulus are disclosed in accordance with embodiments of the present invention. Vertical deflection data is collected along a particular section of railroad track. A first set of vertical track modulus is determined, based in part, on the collected vertical deflection data. At a second time, vertical deflection data is again collected along the particular section of railroad track to be used in determining a second set of vertical track modulus. At least the first and second sets of vertical track modulus are analyzed to determine a mathematical algorithm that facilitates developing a trend in the vertical track modulus of the railroad track.

20 Claims, 20 Drawing Sheets

(56) References Cited

U.S. PATENT DOCUMENTS

| | | |
|---|---|---|
| 5,341,683 A | 8/1994 | Searle |
| 5,386,727 A | 2/1995 | Searle |
| 5,390,544 A | 2/1995 | Madras |
| 5,721,685 A | 2/1998 | Holland et al. |
| 5,753,808 A * | 5/1998 | Johnson .......................... 73/146 |
| 6,044,698 A | 4/2000 | Bryan |
| 6,119,353 A | 9/2000 | Gronskov |
| 6,430,875 B1 | 8/2002 | Clark et al. |
| 6,647,891 B2 | 11/2003 | Holmes et al. |
| 6,742,392 B2 | 6/2004 | Gilmore et al. |
| 7,403,296 B2 | 7/2008 | Farritor et al. |
| 7,755,774 B2 | 7/2010 | Farritor et al. |
| 7,920,984 B2 | 4/2011 | Farritor |
| 7,937,246 B2 | 5/2011 | Farritor et al. |
| 7,942,058 B2 | 5/2011 | Turner |
| 2004/0003662 A1 | 1/2004 | Kenderian et al. |
| 2005/0072236 A1 | 4/2005 | Heyman et al. |
| 2006/0136152 A1 | 6/2006 | Takahashi |
| 2007/0214892 A1 | 9/2007 | Turner et al. |
| 2008/0228436 A1* | 9/2008 | Farritor .......................... 702/150 |
| 2010/0288049 A1 | 11/2010 | Hoyt |
| 2011/0098942 A1 | 4/2011 | Turner |
| 2012/0132005 A1 | 5/2012 | Turner et al. |

OTHER PUBLICATIONS

Lu, S. et al. "Measurement of Vertical Track Modulus From a Moving Railcar," Proceedings of the AREMA 2006 Annual Conference, Louisville, KY, Sep. 17, 2006.

Lu, S. et al., "On the Relationship Between Load and Deflection in Railroad Track Structure," Proceedings of the AREMA 2008 Annual Conference, Salt Lake City, UT, Sep. 21, 2008.

Ghoshal, Goutam et al., "Diffuse Ultrasonic Backscatter in a Two-Dimensional Domain", ACTA Mechanica, vol. 205, No. 1-4, pp. 35-49, Apr. 21, 2009.

International Search Report and Written Opinion issued in PCT/US2011/062383, mailed Mar. 5, 2012, 11 pages.

\* cited by examiner

VERTICAL TRACK MODULUS TRENDING

CROSS-REFERENCE TO RELATED APPLICATIONS

This application is a continuation application of U.S. application Ser. No. 12/206,345, filed Sep. 8, 2008, which claims priority to U.S. Provisional Application No. 60/970,740, filed Sep. 7, 2007, and which is a continuation-in-part application of U.S. application Ser. No. 12/049,805, filed Mar. 17, 2008, which claims priority to U.S. Provisional Application No. 60/894,983, filed Mar. 15, 2007, all of which are incorporated herein by reference in their entirety for all purposes.

STATEMENT REGARDING FEDERALLY SPONSORED RESEARCH OR DEVELOPMENT

This application is funded by Federal Railroad Administration Grant No. DTFR 53-04-G-00011; UNL Account No. (WBS No.) 25-1105-006-002; Principal Investigator Dr. Shane Farritor, et al. The government has certain rights in the invention.

BACKGROUND

The quality of a railroad track is a major factor in railroad safety. One accepted indicator of track quality is the rail's vertical track modulus. As such, it is important to forecast and trend the vertical track modulus.

SUMMARY

Embodiments of the present invention relate to systems and methods for determining a trend in vertical track modulus. Vertical deflection data is collected along a particular section of railroad track. A first set of vertical track modulus is determined, based in part, on the collected vertical deflection data. At a second time, vertical deflection data is again collected along the particular section of railroad track to be used in determining a second set of vertical track modulus. At least the first and second sets of vertical track modulus are analyzed to determine a mathematical algorithm that facilitates developing a trend in the vertical track modulus of the railroad track. In an additional embodiment, a location offset is determined and applied to the first and/or the second set of vertical track modulus to provide location correlated data. In an additional embodiment, an indication is provided that indicates when the vertical track modulus is expected to exceed a predefined threshold.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

Embodiments are described in detail below with reference to the attached drawing figures, wherein.

DETAILED DESCRIPTION

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
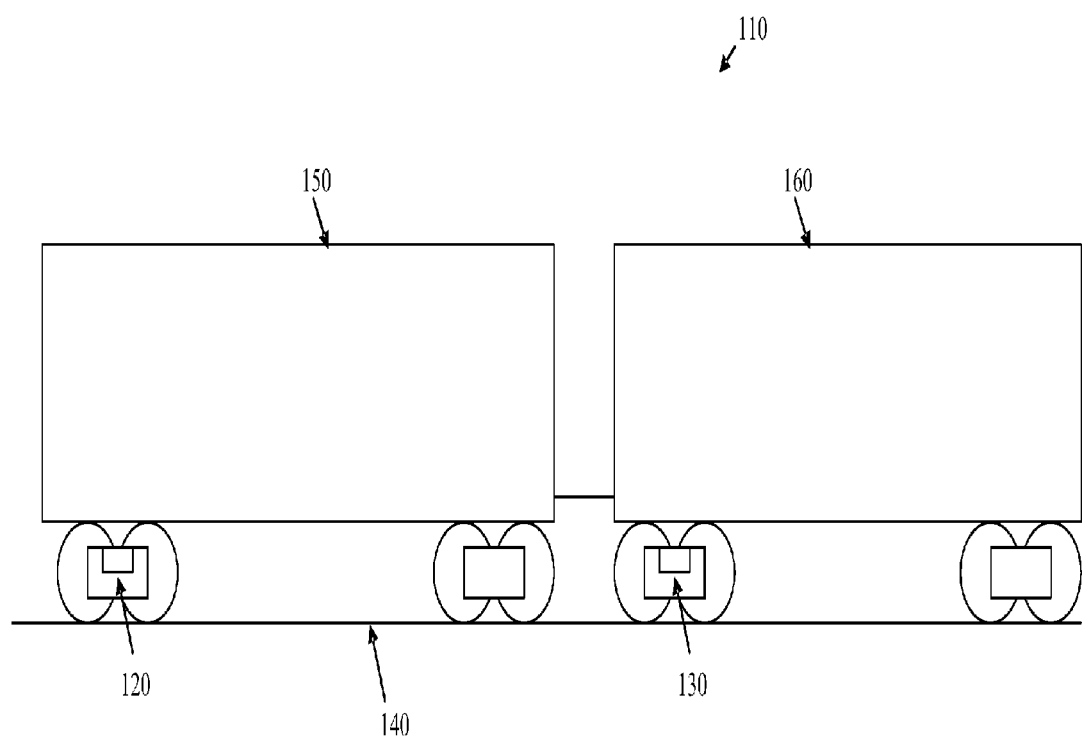
FIG. 1 is an illustration of one embodiment of an on-board, non-contact measurement system of the present invention.

Referring to the drawings in general, and initially to FIG. 1 in particular, an exemplary on-board, non-contact measurement system is shown and designated generally as system 110. System 110 is but one example of a suitable computing environment and is not intended to suggest any limitation as to the scope of use or functionality of the invention. Neither should system 110 be interpreted as having any dependency or requirement relating to any one or combination of components illustrated.

The system 110 measures relative vertical track displacement of a railroad track based, in part, on two position profiles, i.e., space curves. Such relative measurements are combined with an analytical model of the track structure and measured vehicle loads (e.g., weight and dynamic forces) to estimate a vertical track modulus and track stiffness for the track. Vertical track stiffness refers to the ratio of applied load to displacement. A railway track has several components that can contribute to track stiffness including, for example, a rail, subgrade, ballast, subballast, ties, and fasteners. The rail directly supports the train wheels. Such a rail is supported on a rail pad and stabilized with fasteners coupled with crossties. The crossties rest on a layer of rock ballast and subballast such that drainage can occur. The soil below the subballast is referred to as a subgrade.

Track modulus refers to a supporting force per unit length of rail per unit rail deflection. Stated differently, track modulus refers to a coefficient of proportionality between a vertical rail deflection and a vertical contact pressure between the rail base and track foundation. In some embodiments, vertical track modulus does not include the effects of a rail. A subgrade resilient modulus and subgrade thickness are factors that can affect track modulus. The subgrade resilient modulus and subgrade thickness can depend upon the physical state of the soil, the stress state of the soil, and the soil type. Generally, track modulus may increase in instances where subgrade resilient modulus increases. In instances where the subgrade layer thickness increases, the track modulus generally decreases.

In addition, ballast layer thickness and fastener stiffness are also features that can affect track modulus. For example, increasing the thickness of the ballast layer may increase track modulus. Similarly, increasing fastener stiffness might also increase track modulus. Such an increase in track modulus can be caused by the load being spread over a larger area. In some cases, it may be desirable to measure a net effective track modulus. In such a case, each of the factors (e.g., subgrade resilient modulus, subgrade thickness, ballast layer thickness, and fastener stiffness) might be utilized to measure the net effective track modulus.

Track modulus can affect track performance and/or maintenance requirements. In some instances, a low track modulus and large variations in track modulus are undesirable. A low track modulus can cause differential settlement that might increase maintenance needs. Large variations in track modulus, such as variations often found near bridges and crossings, can increase dynamic loading. An increase in dynamic loading can reduce the quality of track components and, thereby, result in shorter maintenance cycles. One skilled in the art will appreciate that reducing variations in track modulus at grade (i.e. road) crossings can lead to an enhanced track performance and reduced track maintenance. Ride quality, as indicated by vertical acceleration, can also be dependent, at least in part, on track modulus.

As higher-speed rail vehicles are oftentimes utilized to address economic constraints of both passenger and freight rail services, an enhanced performance of high-speed trains is beneficial. The performance of high-speed trains can also depend on track modulus. For example, at high speeds, there can be an increase in track deflection caused by larger dynamic forces. Such forces become significant as rail vehicles reach 50 km/hr. One skilled in the art will appreciate that a track with a high and consistent modulus may allow for higher train speeds and an increase in performance and revenue.

To identify portions of a track with reduced performance, measurements of low-track modulus, variable-track modulus, void deflection, variable total deflection, and inconsistent rail deflection can be used. Such measurements are oftentimes expensive. In addition, the measurements are generally made over short distances, such as tens of meters.

Accordingly, a vertical track modulus measurement system is oftentimes desirable such that poor performance can be determined over large sections of a track. In some instances, a trackside measurement approach is utilized to obtain a vertical track modulus. With the trackside approach, a section of track is closed to rail traffic, and a work crew uses specialized equipment to make measurements at various discrete locations. Using the trackside approach, rail deflection can be measured before and after a static "point" load is applied. The trackside approach can include a Beam on Elastic Foundation method and/or a Deflection Basin method.

The Beam on an Elastic Foundation method uses a structural model, such as the Winkler Model, to represent the track system. The Winkler model represents a point load applied to an infinite Bernoulli beam on an infinite elastic foundation. Trackside measurements of the deflection at the point where the load is applied are taken for a known load. A track modulus can then be calculated using the following equation:

$$u = \frac{1}{4}\left(\frac{1}{EI}\right)^{\frac{1}{3}}\left(\frac{P}{w_0}\right)^{\frac{4}{3}} \tag{1}$$

where u is the track modulus, E is the modulus of elasticity of the rail, I is the moment of inertia of the rail, P is the load applied to the track, and $w_0$ is the deflection of the rail at the loading point. The Beam on an Elastic Foundation method can use a single measurement. Such a method can provide information for a single point along the rail. In some cases where multiple loads are present, as with multi-axle railway vehicles used to apply the point load, small deflections can be assumed and superposition may be needed. In such cases, an iterative solution can be utilized, rather than simplifying the Winkler model, as in Equation (1). Because slack in the rail can cause non-linearity in the load/deflection relationship, a small load can be applied to determine the zero displacement position for the measurement. Thereafter, a heavy load can be applied and used as a loaded measurement.

The second trackside method, the Deflection Basin Method, uses a vertical equilibrium of a loaded rail to determine track modulus. In this approach, rail deflection caused by one or more point loads is measured at multiple locations along the rail. The entire deflected "area" can be calculated. Using a force balance, the deflected area, or deflection basin, can be shown to be proportional to the integral of the rail deflection:

$$P = \int_{-\infty}^{\infty} q(x)\,dx = \int_{-\infty}^{\infty} u\delta(x)\,dx = uA_\delta \tag{2}$$

where P is the load on the track, q(x) is the vertical supporting force per unit length, u is the track modulus, δ(x) is the vertical rail deflection, $A_\delta$ is the deflection basin area (area between the original and deflected rail positions), and x is the longitudinal distance along the track. The multiple deflection measurements result in longer traffic delays. Similar to the Beam on an Elastic Foundation method, both heavy and light loads can be used to eliminate slack, which may further increase delays.

Such trackside measurement methods (e.g., Beam on an Elastic Foundation method and Deflection Basin method) can be time consuming and expensive. In addition, a track modulus measured using the trackside measurement methods might be valid for a small length of track.

Accordingly, it is desirable to use an on-board modulus measurement system for determining a vertical track modulus. On-board measurements are made from a moving rail car. As such, on-board measurements can be made with less interruption of rail traffic and over longer distances.

In some cases, on-board systems are labor intensive and move at slow speeds. Thus, such on-board systems might be limited to short distances (e.g. hundreds of meters) and may still interrupt traffic. Such on-board systems use a long, rigid truss that rides on two unloaded wheels. The truss creates a straight line, or cord, that is used as a reference for the measurement. A third wheel may then be used to apply a load at midpoint of the cord (or truss), and the relative displacement between the loaded wheel and the unloaded truss can be measured. The truss should be long enough, generally 30.48 m (100 ft), so that the two endpoints are not affected by the load at the center of the truss. Such an on-board system requires two measurements (e.g., one with a light load, made with a similar truss, and the heavy load) to distinguish between changes in geometry and changes in modulus. The relative displacement of the loaded wheel with respect to the unloaded wheel can be measured and, thereafter, the track modulus can be estimated.

One vehicle, called the Track Loading Vehicle (TLV), uses such an on-board approach. This vehicle is capable of measuring track modulus at speeds of 16.1 km/hr (10 mph). The TLV uses two cars, each with a center load bogie capable of applying loads from 4.45 kN to 267 kN (1 to 60 kips). A light load (13.3 kN or 3 kips) can be applied by the first vehicle while a heavier load is applied by the second vehicle. A laser-based system on each vehicle measures the deflections of the rail caused by the center load bogies. The test procedure involves two passes over a section of track (e.g., first applying a 44.5 kN (10 kip) load and then a 178 kN (40 kip) load). Using the TLV, tests are often performed at speeds below 16.1 km/hr (10 mph) and, accordingly, it is difficult to test long section of track (hundreds of miles). In addition, a significant expense for both equipment and personnel is incurred for operation.

Figure 2:
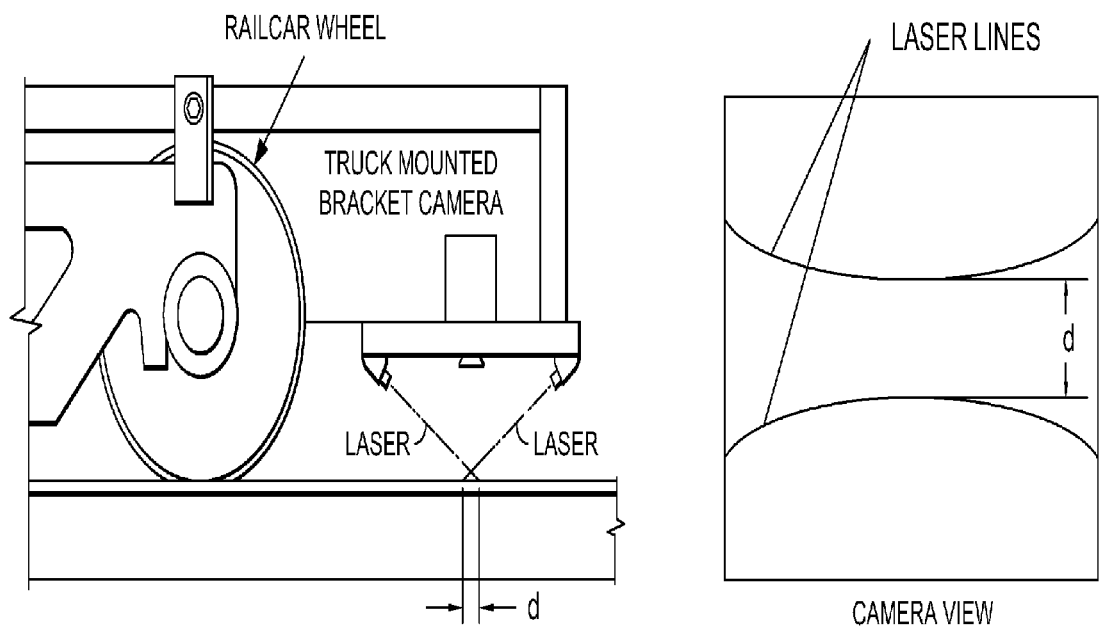
FIG. 2 is a schematic of the modulus measurement system mounted to a train showing an exemplary embodiment of a recent system.
Figure 3:
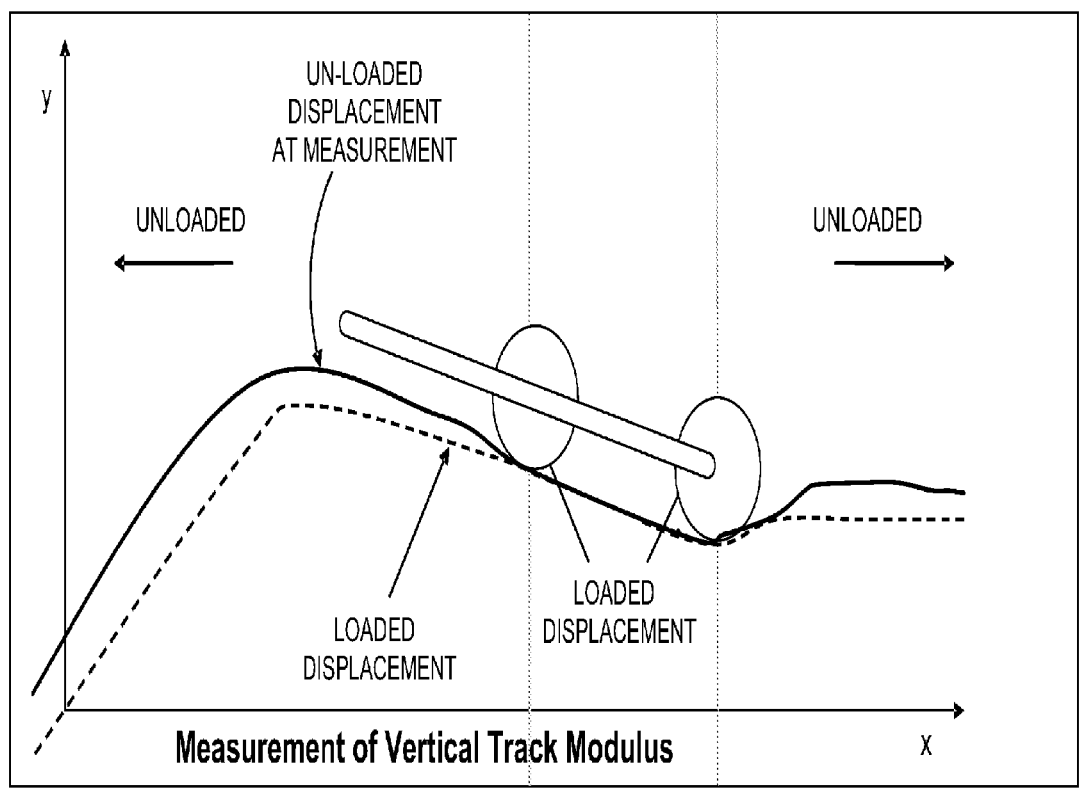
FIG. 3 is an illustration of a recent system measurement of vertical track modulus.

A track modulus may be determined from a moving railcar that operates at higher speeds. The more recent systems are used to measure the relative displacement of a railroad track between a loaded point and an unloaded point, determine the quality of the track, and determine vertical track modulus and vertical track stiffness. Such systems use a rail vehicle having each wheel engage the rail at a wheel and rail contact point. A mechanism is used to measure the vertical displacement of the track at a distance along the rail spaced from one of the wheel and rail contact points. The sensor system includes a digital vision system and two line lasers, as shown in FIG. 2 and FIG. 3. The camera and line lasers are rigidly attached to a bracket mounted to the sideframe (i.e., a structure member that connects axles) of a truck (i.e., two-axle assembly). The lasers are projected at an acute angle, such as 30°. The lasers cross and create curves across the surface of the rail. On softer track, the rail may rise relative to the wheel and rail contact point, and the laser lines, as observed by the camera, may move closer together. Conversely, the distance between the lasers may increase on stiffer track. The minimum distance between these lines, d, can be related mathematically to the track modulus. Using line lasers allows the system to compensate for lateral movement of the rail relative to the camera and for changes in rail profile. This system measures the relative displacement based on the relative displacement between an unloaded point and the line created by the two wheel contact points on a given truck. Upon measuring the relative displacement, the vertical track modulus can be estimated.

Figure 4:
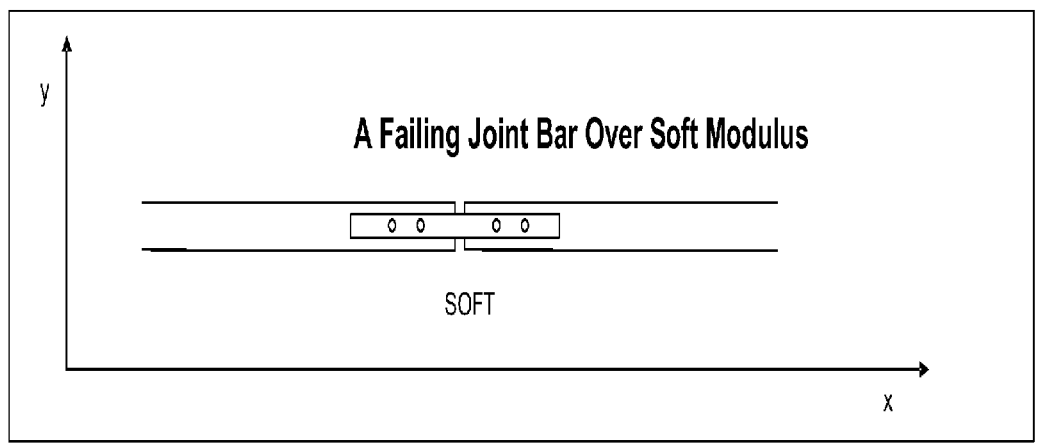
FIG. 4 is an illustration of a failing joint bar over soft modulus.
Figure 5:
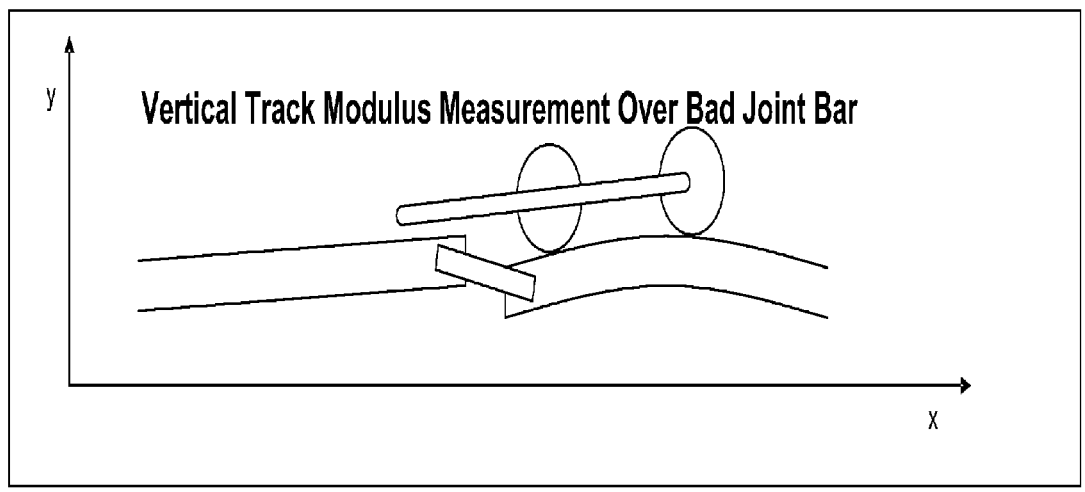
FIG. 5 is an illustration of a measurement of a vertical track modulus over a bad joint bar.
Figure 6:
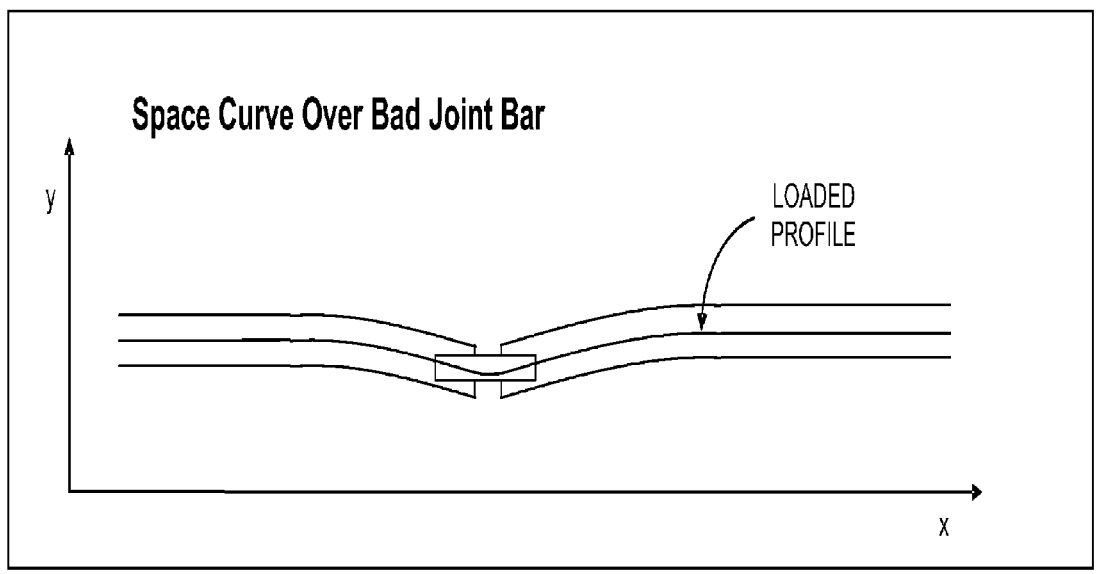
FIG. 6 is an illustration of a space curve over a bad joint bar.

Such a system is useful in situations where there is a weak joint bar over a soft spot (e.g., low modulus), as shown in FIG. 4. The weak joint bar can cause the low modulus or the low modulus can cause the weak joint bar. The weak joint bar and the low modulus may also be unrelated and may be accompanied by a geometry problem. As shown in FIG. 5, this system also compares the loaded end of the rail with a measurement of the relative displacement across the joint bar and, therefore, may find weaknesses in the track that can cause derailments. By contrast, as shown in FIG. 6, a system using space curves provides small displacements and, accordingly, may not find weaknesses in the track that can cause derailments. For example, assume a long section of perfectly uniform track with a low modulus is compared to a long section of uniform track with a high modulus. A space curve measurement might reveal a straight curve, whereas the system of FIG. 5 might show a difference in relative displacement that can show the modulus.

Referring again to FIG. 1, the system 110 comprises a first position sensor 120 and a second position sensor 130 for determining the position profile of a track 140 and a computation system (not shown) for determining the vertical displacement of the track. The first position sensor 120 is attached to rail vehicle 150. The second position sensor 130 is attached to rail vehicle 160. Position sensors 120 and 130 may be attached to the truck of a rail vehicle, a wheel of a rail vehicle, or another component of a rail vehicle. In embodiments where position sensors are mounted to the truck of a rail vehicle, a bracket mounted to a side frame of the truck may be utilized. Regardless of whether a position sensor is attached to the wheel, truck, or other component of a rail vehicle, position sensors 120 and 130 may be mounted vertically, horizontally, or in an alternative orientation.

In one embodiment, two position sensors, such as first position sensor 120 and second position sensor 130, are utilized to determine position profiles of a track. One skilled in the art will recognize that a plurality of position sensors may be utilized to determine position profiles of a track. The two or more attached position sensors are positioned near varying vertical loads. In one embodiment, one rail vehicle may have varying vertical loads. Accordingly, in such an embodiment, two or more position sensors may be attached to one rail vehicle. Alternatively, the two or more position sensors may be attached to separate rail vehicles with each rail vehicle having a different vertical load, e.g., a heavy vertical load and a light vertical load. In such an embodiment, a leading or trailing rail vehicle may be loaded with more or less weight.

Figure 7:
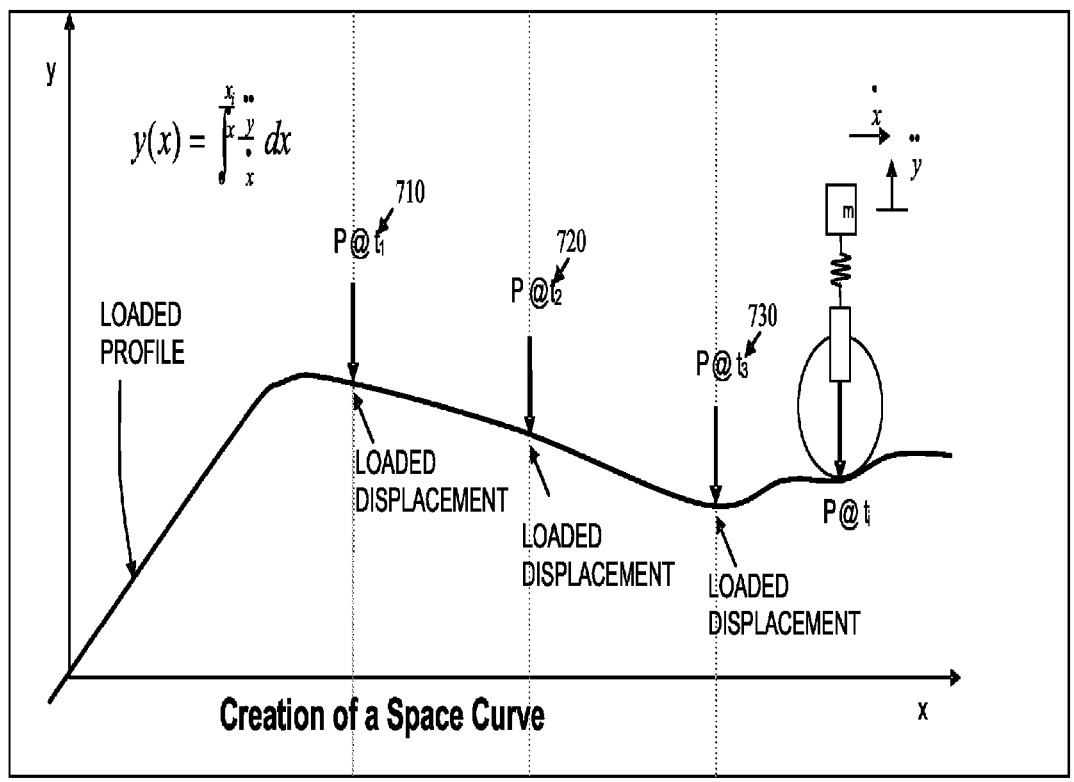
FIG. 7 is an illustration of the creation of a position profile.

As previously mentioned, position sensors 120 and 130 determine at least one position profile of track 140. In one embodiment, position sensors 120 and 130 include an Inertial Measurement Unit or accelerometer. In such an embodiment, to determine a position profile of the track, a position sensor attached to a moving rail vehicle can measure the vertical acceleration, among other accelerations. In some embodiments, the position sensor may not measure an acceleration until the rail vehicle reaches a sufficient speed. With data regarding the time of the measurements and the distance traveled along the tracks, the measured vertical acceleration may be integrated twice to determine the position profile of the track. FIG. 7 illustrates a position profile at a first time 710, a position profile at a second time 720, and a position profile at a third time 730.

The distance traveled along the tracks can be determined by a global positioning system (GPS), an odometer, or other similar device that can be used to measure distances. In an embodiment utilizing an odometer, the odometer may be mounted such that it is observed and its measurements recorded by a camera. In an embodiment utilizing a global positioning system, automatic image geocoding may be used to attach GPS localization to the images. The automatic image geocoding may be done through a GPS receiver plug-in for the camera. The date, time and GPS stamps may be permanent, non-modifiable, intrinsic information that is attached as pixels into the digital images.

Figure 8:
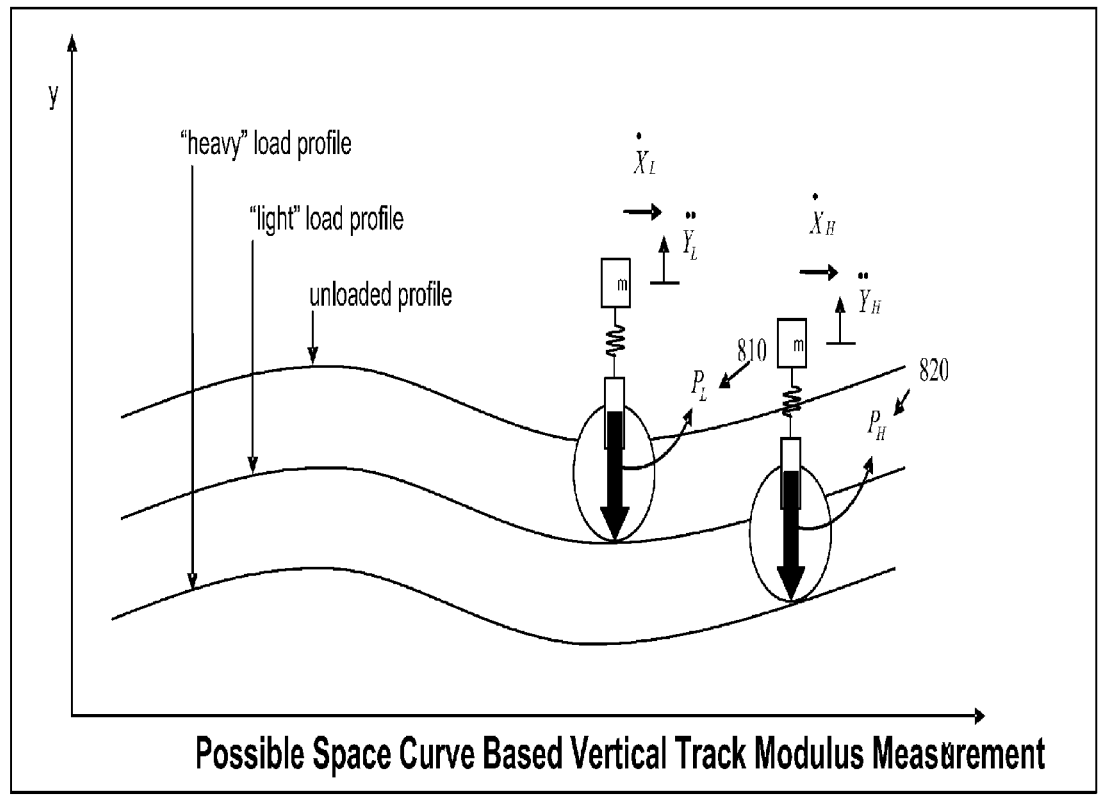
FIG. 8 is an illustration of one embodiment of a position profile based on a vertical track modulus measurement.

The computation system (not shown) determines the vertical displacement between position profiles determined by first position sensor 120 and second position sensor 130. For example, with reference to FIG. 8, the computation system determines the vertical distance between the "light" vertical load 810 and the "heavy" vertical load 820. In some embodiments, to determine vertical displacement, the position of each truck is measured with respect to the vehicle body. In such a case, a relative measurement may then be made using two position profiles and the measured position of each truck with respect to the vehicle body. The computation system may comprise hardware, software, or a combination thereof.

Upon determining the vertical displacement between two position profiles, a vertical track modulus may then be estimated. A mathematical model can be used to calculate the track modulus based on the relative displacement between two position profiles determined by position sensors. For example, the Winkler model, the discrete support (crosstie) model, and the nonlinear stiffness model may be utilized to estimate a vertical track modulus. Such models assume data regarding the rail's elastic modulus and cross-sectional geometry, which may be commonly available.

In one embodiment of the present invention, the system further comprises a computer system to perform one or more aspects of the invention, e.g., store data or perform calculations for particular aspects. The computer system may operate automatically or upon receiving user input to execute or save. In embodiments where the computer system operates automatically, the computer may store data or perform calculations continuously or at predetermined instances.

The memory for storing data may represent the random access memory (RAM) devices comprising the main storage of the respective computer, as well as any supplemental levels of memory, e.g., cache memories, non-volatile or backup memories (e.g., programmable or flash memories), read-only memories, etc. In addition, each memory may be considered to include memory storage physically located elsewhere in a respective computer, e.g., any cache memory, or any storage capacity used as a virtual memory such as in a mass storage device.

The processor may represent one or more processors, e.g., microprocessors. The processor operates under the control of an operating system, and executes or otherwise relies upon various computer software applications, components, programs, objects, modules, data structures, etc. In an embodiment where a computer system is utilized to perform one or more aspects of the invention, accelerations, time of measurements, distance traveled along the tracks, position profiles, vertical load, vertical displacements, vertical track modulus, or a combination thereof may be calculated and stored.

Figure 9:
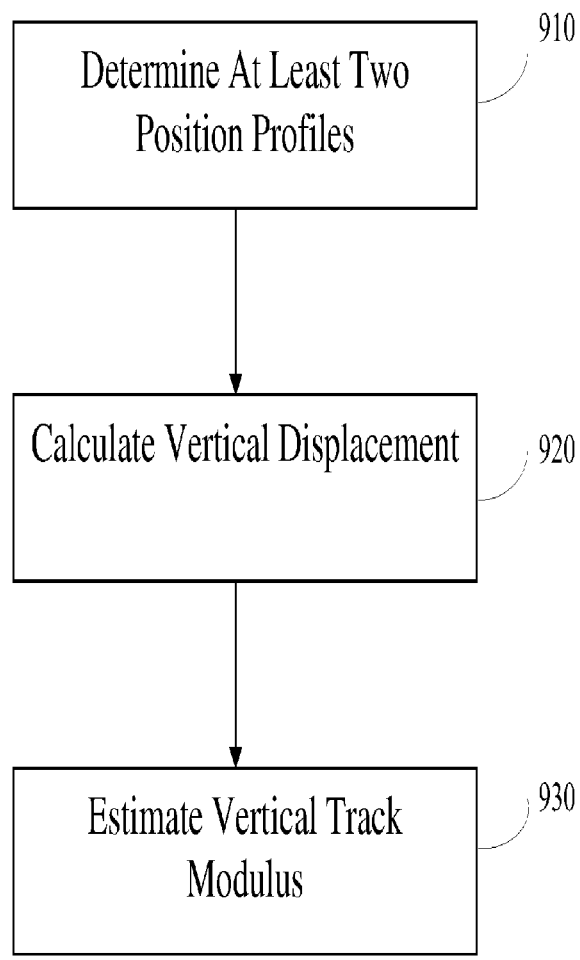
FIG. 9 is a flow diagram illustrating an exemplary method for measuring the relative displacement of a railroad track.

Turning now to FIG. 9, a flow diagram is provided illustrating an exemplary method 900 for measuring the relative displacement of a railroad track. At block 910, two or more profile positions are determined. Each profile position may be determined by a separate position sensor that is attached to a moving rail vehicle. As previously mentioned, in one embodiment, the position sensor measures the vertical acceleration of the moving rail vehicle and, integrates the acceleration twice to determine the position profile of the track. To achieve two or more profile positions, one skilled in the art will appreciate that one rail vehicle having two or more vertical loads may be utilized, two or more rail vehicles have varied vertical loads may be utilized, or a position sensor may be run over the track two or more times. One skilled in the art will further appreciate that measurements may be made at times, days, weeks, months, or even years apart, which may be advantageous to analyzing the trend behavior of a track modulus.

The vertical displacement between the two or more profile positions determined at block 910 is calculated at block 920. At block 930, the vertical track modulus is estimated based on the vertical displacement calculated at block 920. The vertical track modulus may be estimated using a mathematical model such as the Winkler model, the discrete support (crosstie) model, or the nonlinear stiffness model.

Track performance may be measured over time to permit potentially improved prediction of future track behavior. Measurements may be made, for example, at intervals of three months, and these measurements may be used to measure the trend of track performance. Of course, one of ordinary skill in the art will appreciate that other measurement intervals, both longer and shorter than three months, may be used without departing from the scope of the present invention. Accordingly, a measurement made at a first time and a measurement made at a second time may be used to predict track properties at a time subsequent to both the first time and the second time.

For the purpose of such a trending analysis it may be desirable to remove both offsets so that relative comparisons can be made over short sections of track. The relative comparisons would evaluate one measurement relative to a previous measurement made at the same location at an earlier time.

To remove the measurement offset (Yrel) an average may be taken over a distance, such as 0.1 miles, of track. The difference between the two average measurements may then be added to each data point in the lower measurement to effectively shift the data in the vertical direction.

To remove the offset in milepost the cross correlation function may be introduced to mathematically quantify the offset. Cross correlation is a standard method of estimating the degree correlation between two sets of measurements. Consider two series x(i) and y(i) both of length N where i=0, 1, 2 ... N−1. The cross correlation $\hat{R}_{xy}$ at delay m is defined as:

$$\hat{R}_{xy}(m) = \frac{1}{N}\sum_{n=0}^{N-1} x(n)y(n+m), \text{ where}$$

$$m = -(N-1), \ldots, -2, -1, 0, 1, 2, \ldots, N-1$$

For various values of m, $\hat{R}_{xy}$ is in the range $-1 \leq \hat{R}_{xy} \leq 1$. The bounds, −1 and 1, indicate maximum correlation and 0 indicates no correlation. A high negative correlation indicates a high correlation but where one series is the inverse of the other series.

A line or other curve may be fitted to the collected trend data to predict future track performance. Collected data may be from a first time and a second time, or may be from any number of times. Such an approach can predict at what point in the future track performance may fall outside of acceptable parameters.

Figure 10:
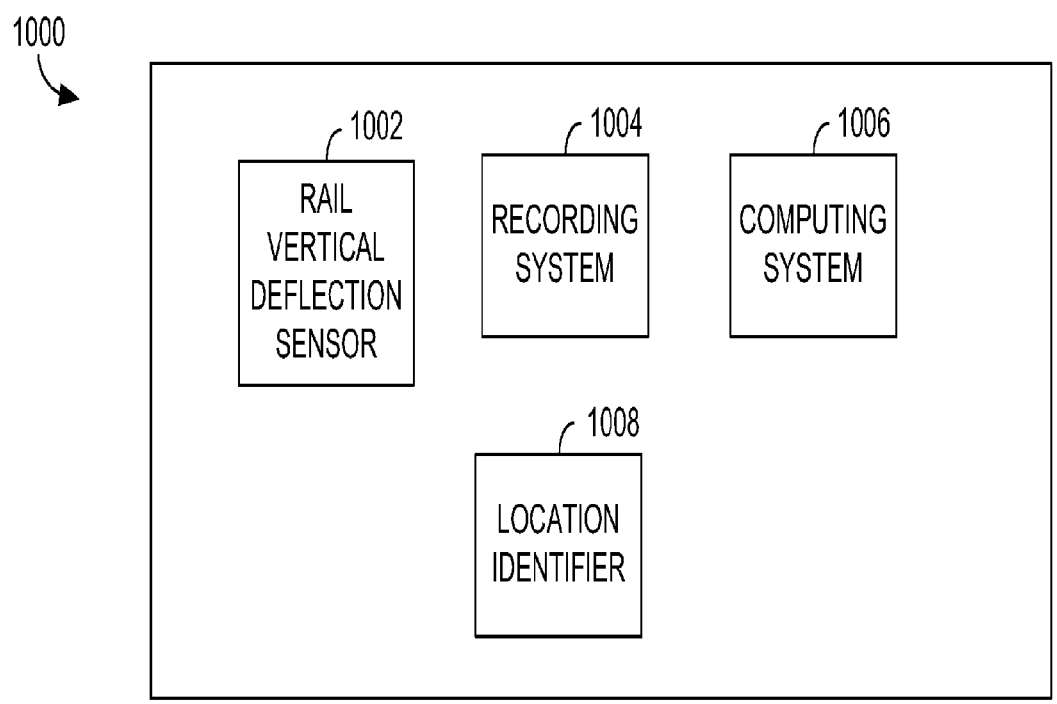
FIG. 10 is a block diagram illustrating a system for estimating vertical track modulus in accordance with embodiments of the present invention.

Turning to FIG. 10, a block diagram is provided illustrating a system 1000 for estimating vertical track modulus in accordance with embodiments of the present invention. It should be understood that this and other arrangements described herein are set forth only as examples. Other arrangements and elements can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown, the system 1000 includes a rail vertical deflection sensor 1002, a recording system 1004, a computing system 1006, and a location identifier 1008. In an embodiment, the rail vertical deflection sensor 1002 is utilized to measure a vertical deflection of a track. The sensor systems discussed with respect to FIG. 1 and FIG. 2 are examples of the rail vertical deflection sensor 1002.

In an embodiment, the vertical deflection data and measurements are stored by the recording system 1004. The recording system 1004 is a computing system as previously discussed. Therefore, in an exemplary embodiment, the recording system includes computer readable storage media that is utilized to store data representing measurements of the vertical deflection of a track. The recording system 1004, in an embodiment, includes a log in which the collected data and/or calculated data is stored. In an embodiment of the present invention, the log is a database that is capable of storing the location, time, and vertical displacement data. Additional data may also be stored by the log. For example, weather conditions, speed, and other conditions collected to determine a trend in the modulus.

The computing system 1006, is a computing system as previously described. In an exemplary embodiment the computing system utilizes two or more vertical deflection measurements to determine a trending algorithm. In an additional embodiment, the computing system 1006 utilizes two or more vertical deflection measurements to determine a track modulus. In yet another exemplary embodiment, the computing system 1006 utilizes two or more vertical track modulus values to determine a trending algorithm. The computing system 1006, in yet another embodiment, is able to identify when a forecasted vertical track modulus will exceed a predefined threshold.

The location identifier 1008 identifies a location. For example, the location identifier 1008, in an embodiment, identifies a location at which a vertical track measurement is collected. The location may be an absolute or relative location. For example, the location identifier 1008, in an embodiment, utilizes technology compatible with a Global Positioning System (GPS). A GPS compatible location identifier 1008 is able to determine the absolute location, such as the longitude and latitude, at which a measurement is collected. In yet another embodiment, the location identifier 1008 utilizes an odometer to identify a location. An odometer may be utilized to provide a relative location, where the location is relative to a known point or location. For example, an odometer may be set to zero at a specific location, such as a milepost along the track, therefore the odometer will provide a distance from the starting location. In yet another embodiment, a combination of technology that is compatible with a GPS and an odometer will be utilized to identify a location.

Figure 11:
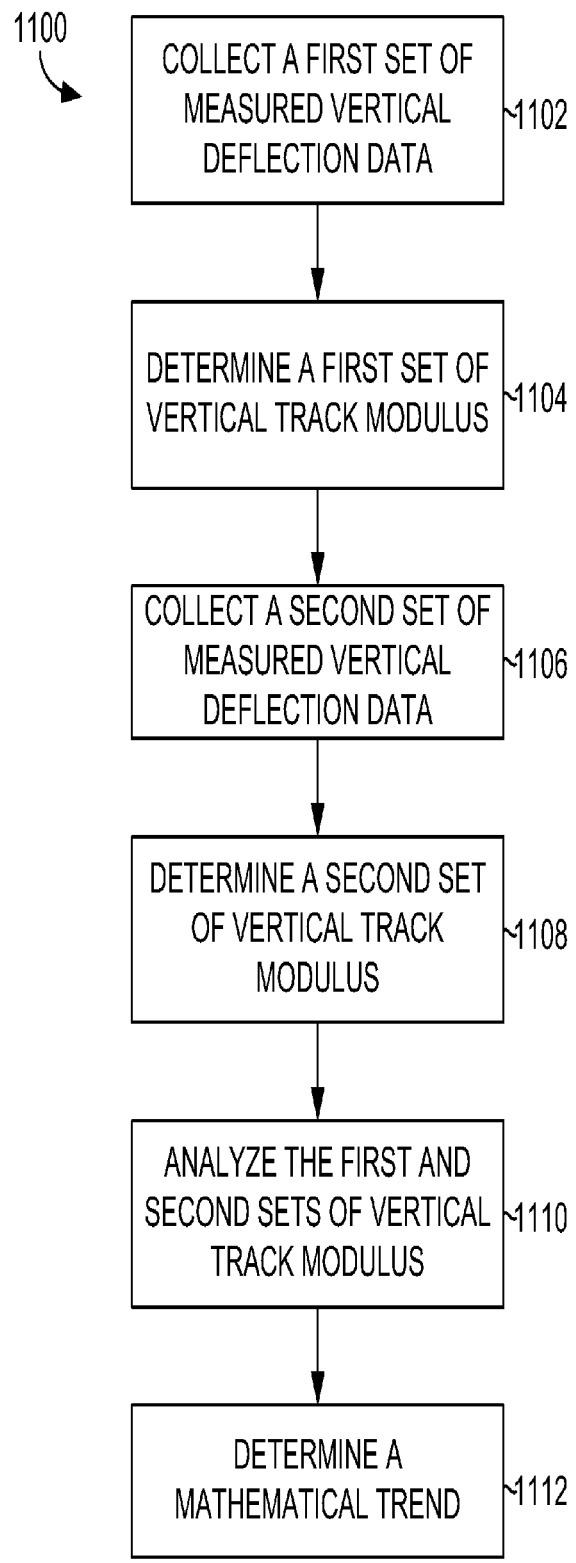
FIG. 11 is a flow diagram illustrating a method for trending vertical track modulus in accordance with embodiments of the present invention.

Turning now to FIG. 11, a flow diagram is provided illustrating a method 1100 for trending vertical track modulus in accordance with embodiments of the present invention. Initially, as shown at a block 1102, a first set of measured vertical deflection data along a portion of railroad track is collected. In an embodiment, the vertical deflection data is collected by a sensor, such as the rail vertical deflection sensor 1002 of FIG. 10. The collection of vertical deflection data in one embodiment is performed by a non-contact sensor, but in an other method the collection of said data is performed by a contact sensor. It is understood that both collection methodologies are within the scope of the present invention. The vertical deflection data, in an embodiment, is recorded and stored in a recording system, such as recording system 1004 of FIG. 10.

As shown at a block 1104, a first set of vertical track modulus is determined. In an exemplary embodiment, the first set of vertical track modulus is determined, based in part, on the first set of measured vertical deflection data. As previously described, a variety of different algorithms and methodologies may be employed to determine the first set of vertical track modulus. For example, the Winkler model is but one methodology that is useable for determining vertical track modulus. In an embodiment, the vertical track modulus is determined by a computing system, such as the computing system 1006 of FIG. 10. The first set of measured vertical deflection data and the resulting first set of vertical track modulus, in an embodiment, are associated with a particular track location at a particular time. Therefore, the first set of vertical track modulus determined at a block 1104 can be compared to vertical track modulus determined for previous or subsequent times. As a result, the first set of vertical track modulus, in combination with either previous or subsequent vertical track modulus are useable to develop a trending algorithm.

A second set of measured vertical deflection data is collected, as shown at a block 1106. In an exemplary embodiment, the second set of measured vertical deflection data is collected for a particular track location that corresponds with a similar particular track location associated with the first set of measured vertical deflection data collected at the block 1102. Continuing with the exemplary embodiment, the second set of measured vertical deflection data is collected at a time subsequent to the first set of measured vertical deflection data, but along a common track location. The second set of measured vertical deflection data is useable for determining a second set of vertical track modulus, as shown at a block 1108.

As shown at a block 1110, the first and second sets of vertical track modulus are analyzed. In an embodiment, the analysis results in a mathematical algorithm that can be graphically charted to represent a trend associated with the track modulus of the particular track location associated with the first and second sets of vertical track modulus. It is within the scope of the present invention to utilize a plurality of sets of vertical track modulus to determine a mathematical algorithm. For example, three or more sets of vertical track modulus may be utilized to develop the mathematical algorithm, resulting in a higher order algorithm and a potentially closer fitting curve.

In an additional embodiment, the analysis of the first and second sets of vertical track modulus includes compensating for a location offset. For example, the precision of the location associated with each set of collected data may allow for a discrepancy between the recorded data for a particular location. This discrepancy is known as a location offset. In an exemplary embodiment, the location offset is identifiable from collected data at a point where an outlier in the data is consistently recorded. For example, an approach to a bridge may include a defining point in vertical deflection measurements where the underlying rail support dramatically changes, resulting in a defining point in the collected data. Continuing with this example, when the track is typically supported by a loose stone aggregate, but the bridge approach is supported by a compacted solid support, such as concrete, the measured vertical deflection data may abruptly change at this particular location. The location associated with the abrupt change will remain constant, but the location identified by a location identifier, such as the location identifier 1008 of FIG. 10, may indicate a discrepancy between data sets. Therefore, the discrepancy between data sets may then be used to correct the location offset of the data sets based on an assumption that the abrupt change in measured vertical deflection occurred at a constant location. It is understood by those with ordinary skill in the art that the previously discussed location offset determination is but one way of determining the location offset.

Figure 18:
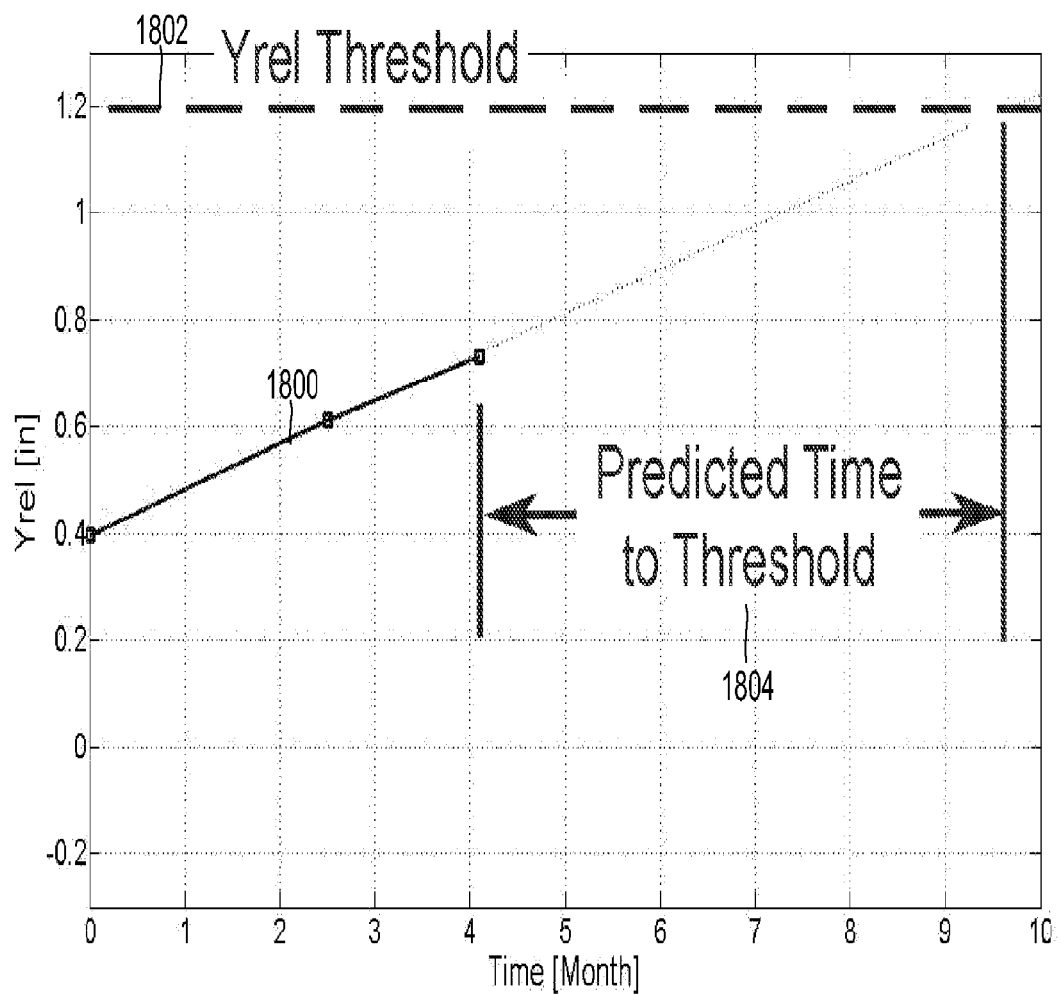
FIG. 18 is an exemplary depiction of a vertical track modulus trend in relation to a predefined threshold.

As shown at a block 1112, a mathematical trend is determined. The mathematical trend is determined based on the analysis illustrated at the block 1110. In an exemplary embodiment, the mathematical algorithm created based on the first and second sets of vertical track modulus is utilized to fit a line or curve. The fitted line or curve represent a mathematical trend that can be utilized to forecast the vertical track modulus. In an additional embodiment, the mathematical trend is analyzed to determine an expected time for the forecasted vertical track modulus to meet or exceed a predefined threshold. For example, turning to FIG. 18, that illustrates an exemplary mathematical trend for vertical track modulus, as generally indicated by the numeral 1800. The trend 1800 provides a visual depiction of the vertical track modulus for a particular location of track. An Yrel threshold 1802 is visually depicted at a value of 1.2 inches. The Yrel threshold 1802 is a predefined threshold at which an indication is provided when the trend 1800 meets or exceeds. A time period 1804 is depicted that indicates that period of time until the vertical track modulus is forecasted to meet or exceed the predefined Yrel threshold 1802. The predefined threshold can be defined at any level of vertical track modulus or vertical deflection that allows the trending algorithm to provide a beneficial result. Therefore, the scope of the present invention is not limited by exemplary predefined threshold indicated within this or other disclosures.

Figure 12:
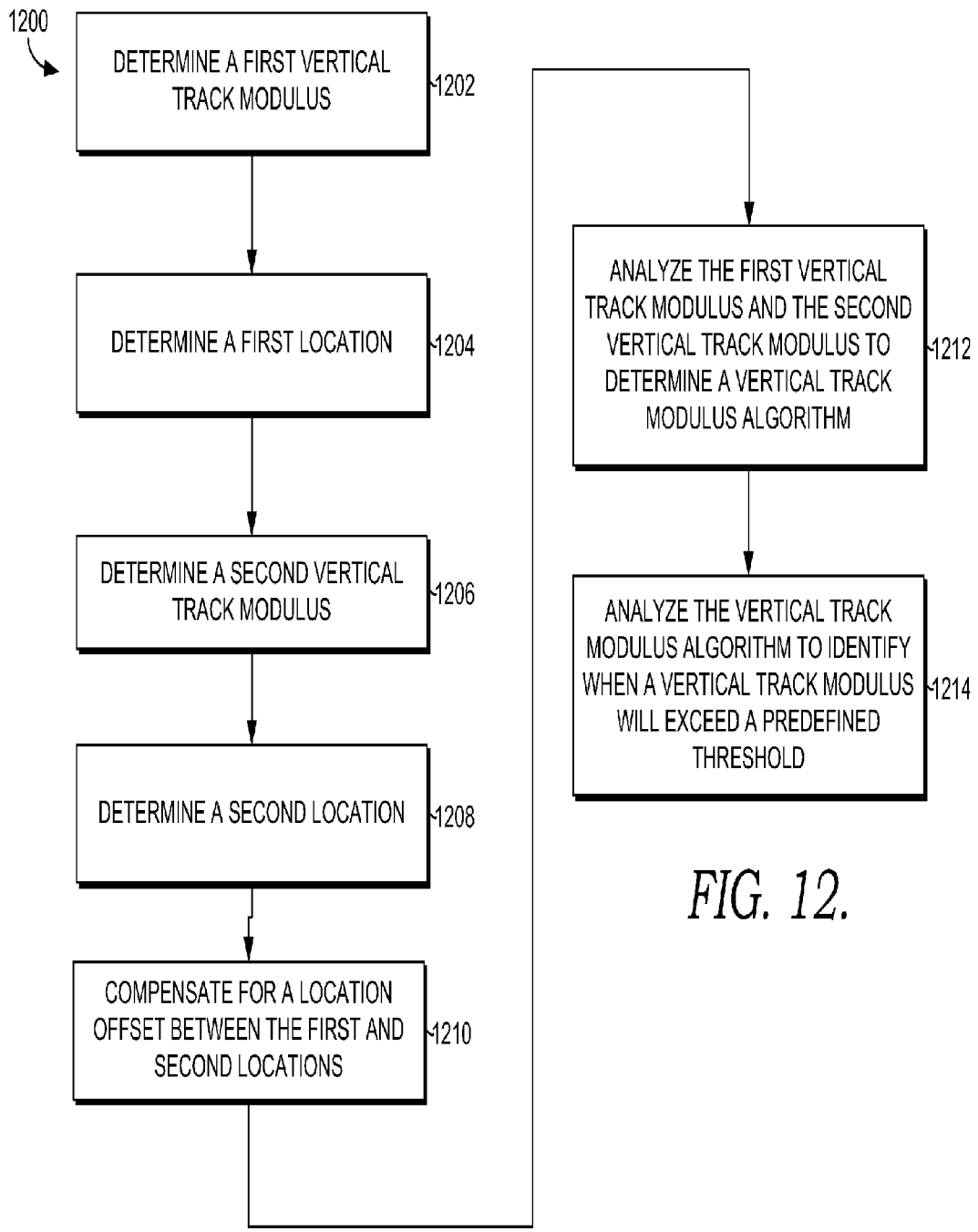
FIG. 12 is a flow diagram illustrating a method for measuring a relative vertical displacement of a railroad track portion utilizing a noncontact measurement system to generate a trend of the vertical track modulus of the railroad track portion in accordance with embodiments of the present invention.

Turning now to FIG. 12, a flow diagram illustrating a method 1200 for measuring a relative vertical displacement of a railroad track portion utilizing a noncontact measurement system to generate a trend of the vertical track modulus of the railroad track portion in accordance with embodiments of the present invention. A first vertical track modulus is determined, as shown at a block 1202. The first vertical track modulus is collected utilizing a noncontact measurement system, such as the system previously discussed with respect to FIGS. 1 and 2. A first location is determined, as shown at the block 1204. The first location is associated with the first vertical track modulus. A second vertical track modulus is determined, as shown at a block 1206. Additionally, a second location is determined, as shown at a block 1208. In an exemplary embodiment, the first and second locations are similar locations along a particular portion of railroad track. Further, in an additional embodiment, the first vertical track modulus and the second vertical track modulus are based, in part, on vertical track measurements that were collected at different times. For example, the first vertical track modulus and the second vertical track modulus represent a three month period of time that has elapsed between measurement of their respective vertical rail displacement.

As shown at a block 1210, a location offset between the first and the second locations is compensated. For example, the compensation of the location offset allows for vertical track modulus, while indicated at different locations, to be correlated based on actual location rather than recorded location. This is because the recorded location is not always an accurate indication of the actual associated location.

The first vertical track modulus and the second vertical track modulus are analyzed to determine a vertical track modulus algorithm, as shown in a block 1212. As previously discussed, the vertical track modulus algorithm provides a mathematical solution for fitting a line or curve to a trend in the vertical track modulus of a particular location of track. The vertical track modulus algorithm may therefore be analyzed to identify when a vertical track modulus will exceed a predefined threshold, as shown at a block 1214. The determination of when a vertical track modulus is expected to meet or exceed a predefined threshold allows for maintenance and repair to be scheduled and budgets to be established.

Figure 13:
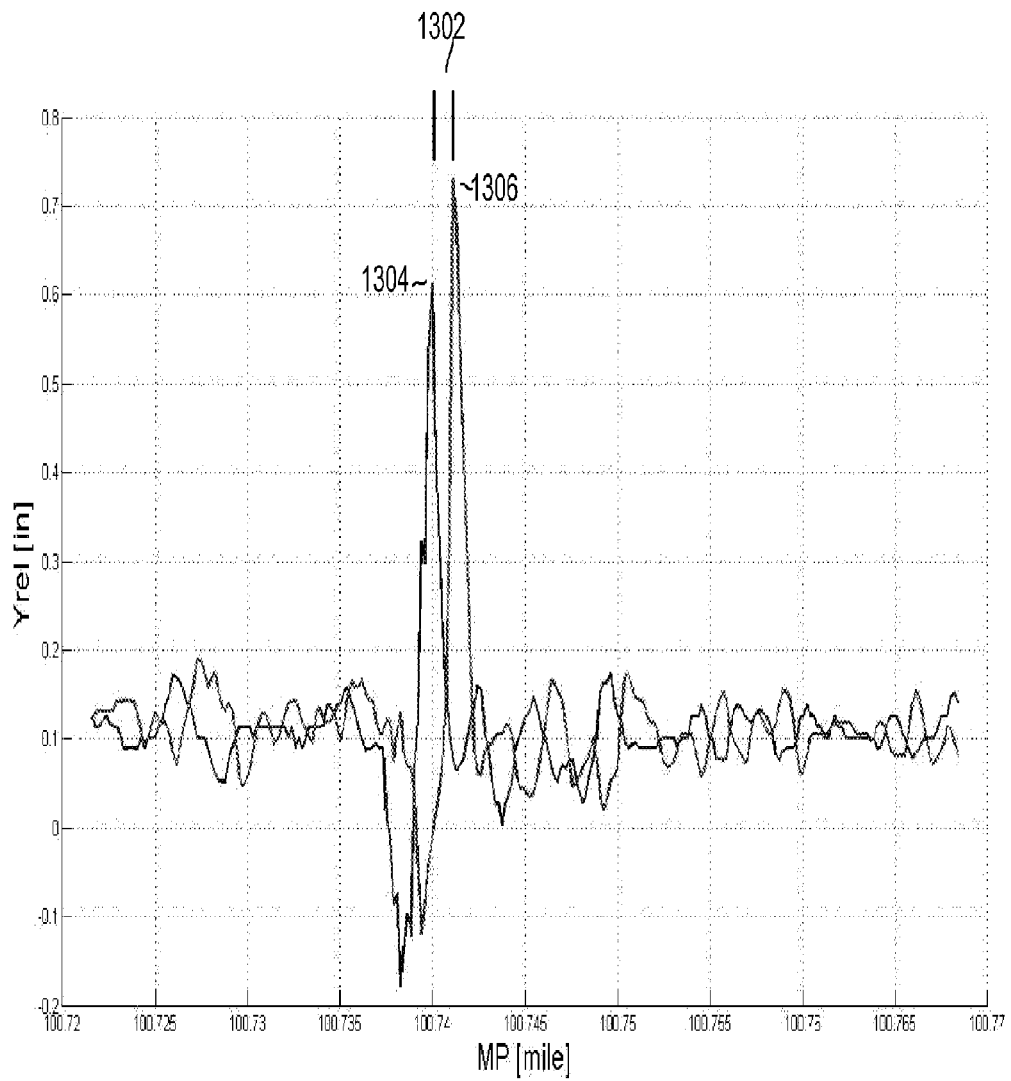
FIG. 13 is a exemplary graphical depiction of two vertical track modulus sets not corrected for location offset.
Figure 14:
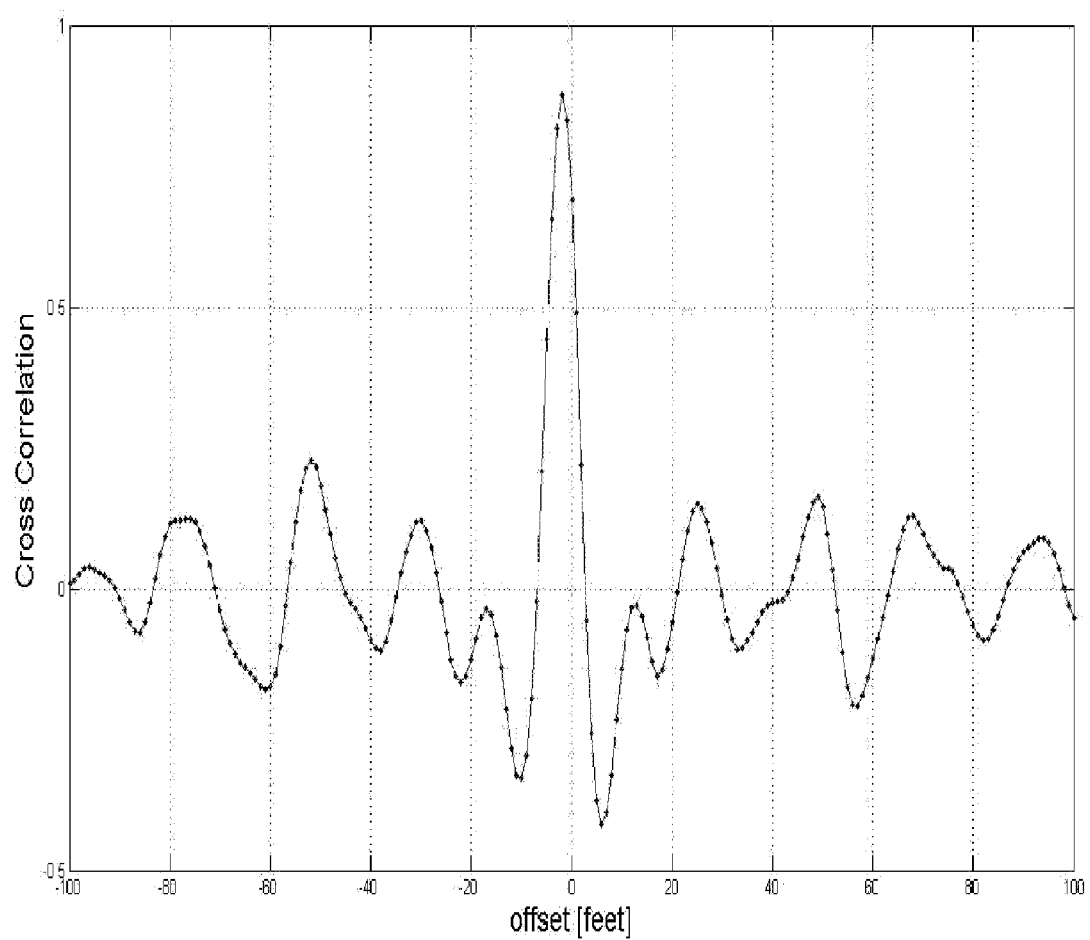
FIG. 14 is an exemplary graphical depiction of a calculated location offset between two sets of vertical track modulus.
Figure 15:
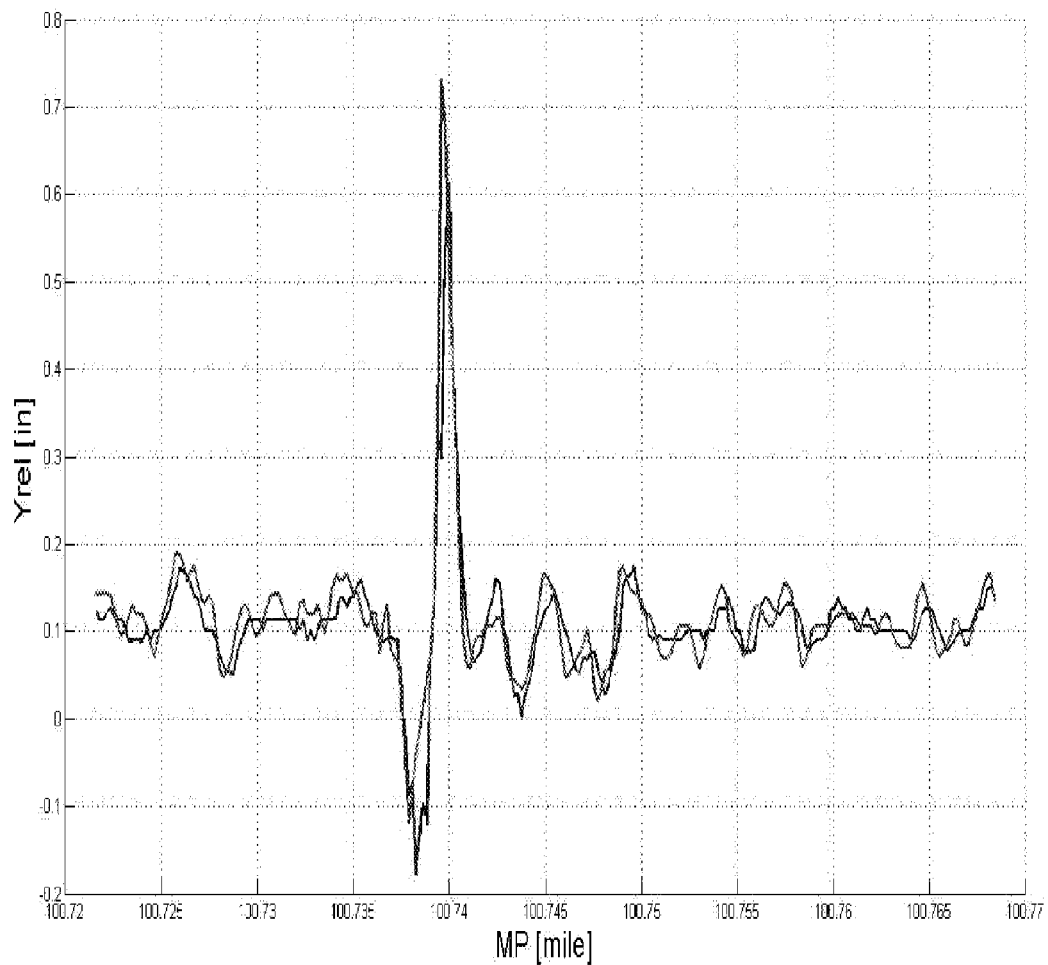
FIG. 15 is an exemplary graphical depiction of two vertical track modulus sets corrected for location offset.

Turning to FIG. 13, a graph of two vertical track deflection modulus along a section of track in accordance with embodiments of the present invention. A location offset 1302 is visually identifiable as a result of a correlation between a first set of data 1304 and a second set of data 1306. In an exemplary embodiment of the present invention, the location offset 1302 will be utilized to correlate the two vertical deflection modulus along the section of track. Turning to FIG. 14, a cross correlation graph between the first set of data 1304 as depicted at FIG. 13 and the second set of data 1306 as depicted at FIG. 13. The graph of FIG. 14 is an exemplary tool that allows for the determination of the location offset. Turning to FIG. 15, a graph of the first set of raw data 1304 of FIG. 13 and the second set of raw data 1306 of FIG. 13 adjusted for the location offset 1302 of FIG. 13.

Figure 16:
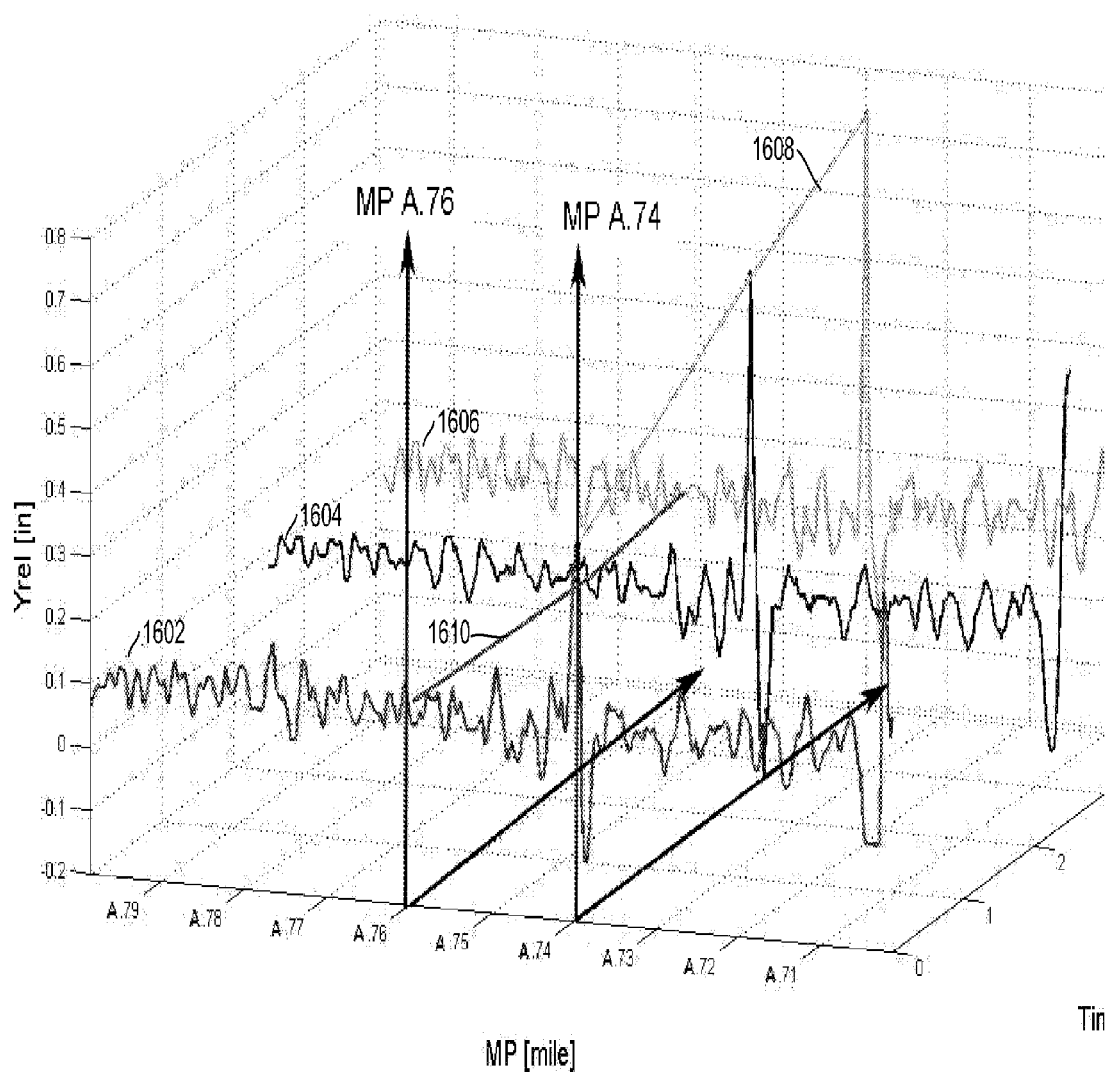
FIG. 16 is an exemplary graphical depiction of three vertical track modulus sets.

Turning to FIG. 16, a graph representing three sets of vertical track modulus. A first set of data 1602, a second set of data 1604, and a third set of data 1606 of vertical track modulus all correlated based on a location that has been corrected for one or more location offsets. In an exemplary embodiment, the sets of data 1602, 1604, and 1606 are based on vertical deflection data recorded at different times. For example, the first set of data 1602 is collected in December of year 1, the second set of data 1604 is collected in February of year 2 (approximately 2 months subsequent to the first set of data 1602), and the third set of data 1606 is collected in April of year 2. As a result of the three set of data 1602, 1604, and 1606, a mathematical algorithm for trending the vertical track modulus can be determined. For example, trend 1608 represents an increasing vertical track modulus at a particular location, such as a milepost A.74. Additionally, another trend line 1610 represents a track modulus trend at another location, such as milepost A.76.

Figure 17:
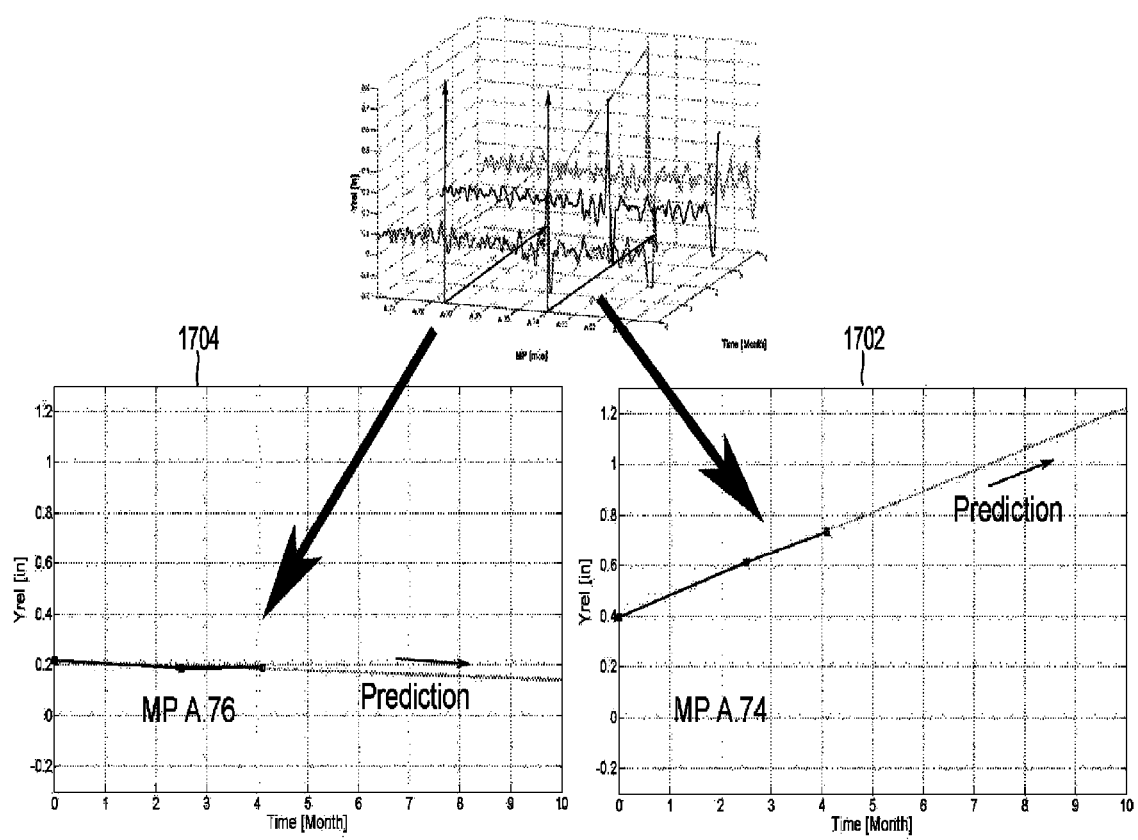
FIG. 17 is an exemplary alternative perspectives of two identified trends related to vertical track modulus.

Turning to FIG. 17, a representation of the graph illustrated in FIG. 16 along with dissected views of trends 1610 and 1608 of FIG. 16. A graph 1704 provides an alternative perspective of trend 1610 of FIG. 16, wherein the graph 1704 includes a graphical forecast of the vertical track modulus for a particular location. A graph 1702 provides an alternative perspective of trend 1608 of FIG. 16, wherein the graph 1702 includes a graphical forecast of the vertical track modulus for a particular location.

Figure 19:
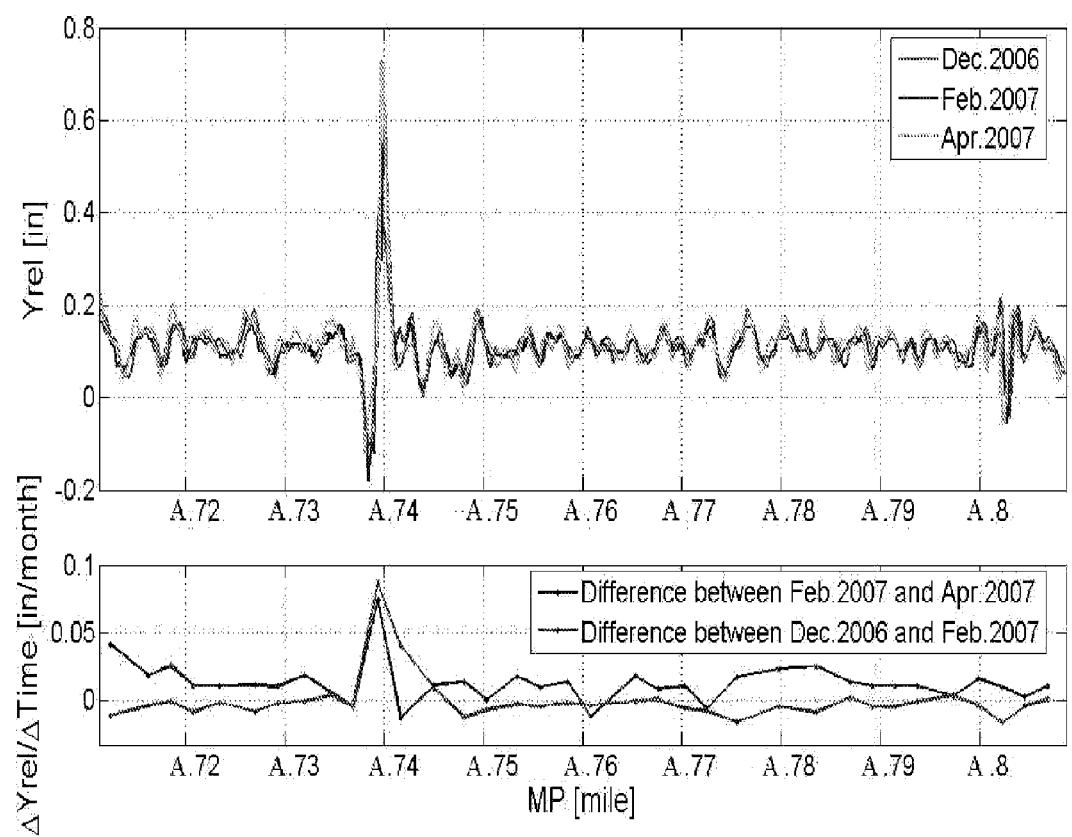
FIG. 19 is another exemplary graphical depiction of three sets of vertical track modulus.
Figure 20:
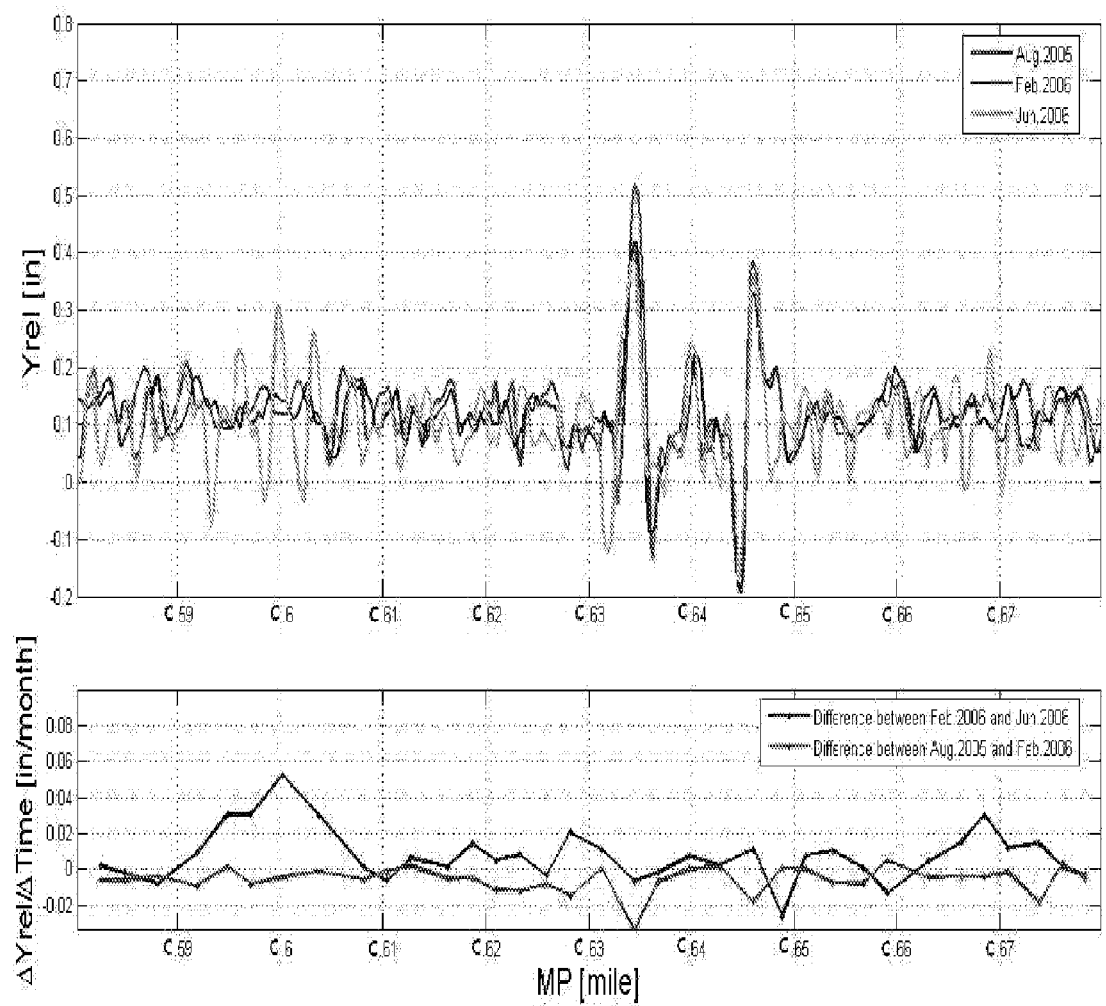
FIG. 20 is yet another exemplary graphical depiction of three sets of vertical track modulus.

Turning to FIG. 19, an alternative perspective of sets 1602, 1604, and 1606 of FIG. 16, in accordance with embodiments of the present inventions. Turning to FIG. 20, a graphical representation of data collected at three times along a particular portion of railroad track.

It is to be understood that the specific embodiments of the present invention that are described herein are merely illustrative of certain applications of the principles of the present invention. It will be appreciated that, although an exemplary embodiment of the present invention has been described in detail for purposes of illustration; various modifications may be made without departing from the spirit and scope of the invention. Therefore, the invention is not to be limited except as by the appended claims.

What is claimed is:

1. A system for estimating vertical track deflection of a railroad track, the system comprising:
   a rail vertical deflection sensor configured for measuring vertical track deflection data along a portion of the railroad track; and
   a computing device configured for trending vertical track data based on two or more vertical track deflection data measurements obtained at different times along a the portion of the railroad track, wherein the computing device is configured to forecast a future vertical track modulus based on the two or more vertical track deflection data measurements obtained over time.

2. The system of claim 1, wherein the computing device is configured to generate a notification indicating when a future vertical track modulus is forecast to exceed a predefined threshold.

3. The system of claim 1, further comprising a location identifier configured for identifying location data along the railroad track associated with the vertical track deflection data measured by the rail vertical deflection sensor.

4. The system of claim 3, wherein the location identifier comprises an odometer.

5. The system of claim 3, wherein the location identifier comprises a Global Positioning System.

6. The system of claim 1, further comprising a means for recording vertical track deflection data.

7. The system of claim 6, wherein the recorded vertical track deflection data is associated with location data identified by the location identifier.

8. The system of claim 6, wherein the means for recording vertical track deflection data comprises a log configured for storing location, time, and vertical displacement data.

9. The system of claim 6, wherein the means for recording vertical track deflection data comprises a log configured for storing location, time, and vertical displacement data.

10. A system for estimating vertical track deflection of a railroad track, the system comprising:
    a rail vertical deflection sensor configured for measuring vertical track deflection data along a portion of the railroad track; and
    a computing device configured for trending vertical track data based on two or more vertical track deflection data measurements obtained at different times along the portion of the railroad track, the system further comprising a means for generating a graphical forecast of the vertical track data along the railroad track.

11. The system of claim 10, further comprising a location identifier configured for identifying location data along the railroad track associated with the vertical track deflection data measured by the rail vertical deflection sensor.

12. The system of claim 11, wherein the location identifier comprises a Global Positioning System.

13. The system of claim 11, wherein the location identifier comprises an odometer.

14. The system of claim 10, further comprising a means for recording vertical track deflection data.

15. The system of claim 14, wherein the recorded vertical track deflection data is associated with location data identified by the location identifier.

16. The system of claim 14, wherein the means for recording vertical track deflection data comprises a log configured for storing location, time, and vertical displacement data.

17. The system of claim 14, wherein the means for recording vertical track deflection data comprises a log configured for storing location, time, and vertical displacement data.

18. A system for estimating vertical track deflection of a railroad track, the system comprising:
    a rail vertical deflection sensor configured for measuring vertical track deflection data along a portion of the railroad track;
    a means for recording vertical track deflection data; and
    a means for trending vertical track data based on two or more vertical track deflection data measurements obtained at different times along the portion of the railroad track, the system further comprising a means for forecasting a future vertical track modulus based on the two or more vertical track deflection data measurements obtained over time.

19. A system for estimating vertical track deflection of a railroad track, the system comprising:
    a first position sensor configured for sensing a first position profile of a rail vehicle engaging the railroad track;
    a second position sensor configured for sensing a second position profile of a rail vehicle engaging the railroad track;
    a means for determining the relative vertical displacement of the railroad track based at least in part on the first and second sensed position profiles; and
    a means for trending vertical track data based on two or more vertical track deflection data measurements obtained along the a portion of the railroad track overtime, wherein the first and second position profiles are associated with a single rail vehicle having first and second vertical loads.

20. A system for estimating vertical track deflection of a railroad track, the system comprising:
    a first position sensor configured for sensing a first position profile of a rail vehicle engaging the railroad track;
    a second position sensor configured for sensing a second position profile of a rail vehicle engaging the railroad track;
    a means for determining the relative vertical displacement of the railroad track based at least in part on the first and second sensed position profiles; and
    a means for trending vertical track data based on two or more vertical track deflection data measurements obtained along the a portion of the railroad track over time, wherein the first position profile is associated with a first rail vehicle having a first vertical load, and wherein the second position profile is associated with a second rail vehicle having a second vertical load.

* * * * *